US012569138B2

(12) United States Patent
Buckley

(10) Patent No.: US 12,569,138 B2
(45) Date of Patent: Mar. 10, 2026

(54) METHODS AND SYSTEMS FOR ANALYZING SURGICAL SMOKE USING ATOMIC ABSORPTION SPECTROSCOPY

(71) Applicant: Stryker European Operations Limited, Carrigtwohill (IE)

(72) Inventor: Kevin Buckley, Cobh (IE)

(73) Assignee: Stryker European Operations Limited, Carrigtwohill (IE)

( * ) Notice: Subject to any disclaimer, the term of this patent is extended or adjusted under 35 U.S.C. 154(b) by 982 days.

(21) Appl. No.: 17/657,672

(22) Filed: Apr. 1, 2022

(65) Prior Publication Data
US 2022/0313300 A1      Oct. 6, 2022

Related U.S. Application Data

(60) Provisional application No. 63/170,262, filed on Apr. 2, 2021.

(51) Int. Cl.
*A61B 5/00*          (2006.01)
*A61B 17/00*          (2006.01)
(Continued)

(52) U.S. Cl.
CPC ....... *A61B 5/0075* (2013.01); *G01N 21/3103* (2013.01); *A61B 2017/00061* (2013.01);
(Continued)

(58) Field of Classification Search
None
See application file for complete search history.

(56) References Cited

U.S. PATENT DOCUMENTS 4,839,143 A      6/1989   Vora et al.
5,200,345 A      4/1993   Young
(Continued)

FOREIGN PATENT DOCUMENTS

CN          102967613 A  *  3/2013
WO      2014142927 A1      9/2014
(Continued)

OTHER PUBLICATIONS

US 10,504,709 B2, 12/2019, Karanesi et al. (withdrawn)
(Continued)

*Primary Examiner* — Sean W Collins
*Assistant Examiner* — Nora W Rhodes
(74) *Attorney, Agent, or Firm* — Howard & Howard Attorneys PLLC

(57) ABSTRACT

A neurosurgery system for resecting tissue after administration of a contrast agent to a patient, the system including an electrosurgical instrument for manipulating tissue which generates a fluid sample from the tissue during ablation, an aspiration channel configured to obtain the fluid sample, an analyzer for analyzing the fluid sample, an indicator configured to provide an indication of the presence of a rare earth metal, and a controller configured to instruct the indicator to provide the indication of the presence of the rare earth metal. The analyzer includes a collector coupled to the aspiration channel and configured to receive a portion of the fluid sample from the aspiration channel, a heater configured to atomize the portion of the fluid sample, and a detector configured to measure an absorption of a wavelength corresponding to a rare earth metal.

20 Claims, 10 Drawing Sheets

(51) Int. Cl.

| | |
|---|---|
| *A61B 18/14* | (2006.01) |
| *G01N 21/31* | (2006.01) |

(52) U.S. Cl.
CPC ..... *A61B 18/1442* (2013.01); *A61B 2576/026* (2013.01); *G01N 2021/3125* (2013.01)

(56) References Cited

U.S. PATENT DOCUMENTS

| | | | |
|---|---|---|---|
| 5,314,827 | A | 5/1994 | Schmidt et al. |
| 5,869,344 | A | 2/1999 | Linforth et al. |
| 6,497,715 | B2 | 12/2002 | Satou |
| 6,504,149 | B2 | 1/2003 | Guevremont et al. |
| 6,955,680 | B2 | 10/2005 | Satou et al. |
| 6,984,220 | B2 | 1/2006 | Wuchinich |
| 7,725,160 | B2 | 5/2010 | Weber |
| 8,267,934 | B2 | 9/2012 | Earley et al. |
| 8,361,070 | B2 | 1/2013 | Hanlon et al. |
| 8,721,638 | B2 | 5/2014 | Deutscher et al. |
| 8,970,840 | B2 | 3/2015 | Kulkarni et al. |
| 9,046,448 | B2 | 6/2015 | Takats |
| 9,053,914 | B2 | 6/2015 | Pringle et al. |
| 9,066,658 | B2 | 6/2015 | Hamel et al. |
| 9,216,051 | B2 | 12/2015 | Fischer et al. |
| 9,255,907 | B2 | 2/2016 | Heanue et al. |
| 9,287,100 | B2 | 3/2016 | Szalay et al. |
| 9,874,655 | B2 | 1/2018 | Daito et al. |
| 2002/0173786 | A1* | 11/2002 | Kortenbach ........... A61B 10/06 606/49 |
| 2007/0114394 | A1 | 5/2007 | Combs et al. |
| 2011/0007312 | A1 | 1/2011 | Bushaw et al. |
| 2014/0194749 | A1* | 7/2014 | Fixler .................. A61B 5/0075 600/473 |
| 2014/0276775 | A1 | 9/2014 | Funk et al. |
| 2014/0293091 | A1 | 10/2014 | Rhoads et al. |
| 2016/0022816 | A1 | 1/2016 | Funk et al. |
| 2018/0057852 | A1 | 3/2018 | Takats et al. |
| 2018/0344993 | A1 | 12/2018 | Ganz et al. |
| 2019/0157059 | A1 | 5/2019 | Jones et al. |
| 2019/0267221 | A1 | 8/2019 | Pringle et al. |
| 2020/0100849 | A1 | 4/2020 | Malackowski et al. |
| 2021/0212751 | A1* | 7/2021 | Ding .................. A61B 18/1445 |
| 2021/0290292 | A1 | 9/2021 | Joseph et al. |
| 2021/0290297 | A1 | 9/2021 | Lennartz et al. |
| 2021/0295990 | A1 | 9/2021 | Joseph et al. |
| 2022/0268784 | A1 | 8/2022 | Schiavinato Eberlin et al. |

FOREIGN PATENT DOCUMENTS

| | | | | |
|---|---|---|---|---|
| WO | WO-2016142689 | A1* | 9/2016 | ............. A61B 1/041 |
| WO | 2019122358 | A2 | 6/2019 | |
| WO | 2019229470 | A1 | 12/2019 | |
| WO | 2020068756 | A1 | 4/2020 | |

OTHER PUBLICATIONS

US 10,777,399 B2, 09/2020, Pringle et al. (withdrawn)

Lacroix, M. et al., "A Multivariate Analysis of 416 Patients with Gliobastoma Multiforme: Prognosis, Extent of Resection, and Survival", Journal of Neurosurgery, vol. 95, No. 2, 2001, pp. 190-198.

Stummer, W. et al., Fluorescence-Guided Surgery with 5-Aminolevulinic Acid for Resection of Malignant Glioma: A randomised Controlled Multicentre Phase III Trial, The Lancet Oncology, vol. 7, No. 5, 2006, pp. 392-401.

Stummer, W., et al., "Extent of Resection and Survival in Glioblastoma Multiforme: Identification of and Adjustment for Bias", Neurosurgery, vol. 62, No. 3, 2008, pp. 564-576.

Valdes, Pablo et al., "Gadolinium-and 5-aminolevulinic Acid-Induced Protoporphyrin IX Levels in Human Gliomas: an Ex Vivo Quantitative Study to Correlate Protoporphyrin IX Levels and Blood-Brain Barrier Breakdown", Journal of Neuropathy & Experimental Neurology, vol. 71, No. 9, 2012, pp. 806-813.

Valdes, Pablo et al., "Quantitative Fluorescence Using 5-aminolevulinic Acid-Induced Protoporphyrin IX Biomarker as a Surgical Adjunct in Low-Grade Glioma Surgery", Journal of Neurosurgery, vol. 123, No. 3, 2015, pp. 771-780.

YouTube, "iKnife: the Surgical Device that Sniffs Out Cancer Video", https://www.youtube.com/watch?v=dBA5V6SRRJQ, Aug. 16, 2018, 3 pages.

\* cited by examiner

160

8B

METHODS AND SYSTEMS FOR ANALYZING SURGICAL SMOKE USING ATOMIC ABSORPTION SPECTROSCOPY

CROSS-REFERENCE TO RELATED APPLICATIONS

This application claims priority to and all the benefits of U.S. Provisional Patent Application No. 63/170,262, filed on Apr. 2, 2021, the disclosure of which is hereby incorporated by reference.

BACKGROUND

A surgical procedure, more specifically tumor resection, is often performed to resect the tumor. Healthcare professionals aim to resect as much of the tumor tissue as possible. The goal of the surgical procedure is to achieve gross total resection (GTR).

Tumor resection involves the removal of cancerous or abnormal tissue and any tumor tissue left behind can lead to local recurrence. Current surgical systems and methods rely on the healthcare professional's ability to differentiate tumor tissue from non-tumorous or normal tissue using their trained eyes and sometimes with the help of an operating microscope and/or diagnostic imaging from scans performed before surgery to remove the tumor tissue. Healthcare professionals may still have to rely on their own ability to sense the subtle changes in color, texture, and/or mechanical properties to identify that a tissue is cancerous or abnormal and should be removed.

There have been numerous technologies developed to help assist the healthcare professional in finding tumor tissue and identifying a tumor margin. Diagnostic imaging techniques, such as magnetic resonance imaging (MRI), x-ray, nuclear radiopharmaceutical imaging, ultraviolet/visible/infrared light, and ultrasound, have been used to acquire anatomical, physiological, and biochemical information images of a body interior. In particular, MRI images may be used to show a contrast between tissues which occurs between areas where water can diffuse freely and areas where the diffusion is restricted. The changes to these diffusion properties that are brought about by disease are often subtle. Thus, contrast agents can be introduced to amplify these changes in MRI images.

Modern surgical techniques for performing tissue resection involve a variety of surgical instruments. Some of those instruments generate smoke and fumes that may be used to differentiate between tumor tissue and non-tumorous tissue. Spectroscopy and/or spectrometry technology combined with surgical instruments have been developed to aid the healthcare professional in distinguishing cancerous tissue and provide intra-operative identification of target substances. For example, ionization mass spectrometry has been used where surgical smoke is transported to a mass spectrometer for mass spectrometric analysis. The mass spectrometric analysis generates one or more mass spectra for the surgical smoke, which are then analyzed to identify the tissue metabolites and classify the tissue substance based on its mass. Such systems including ionization mass spectrometry are expensive to implement and the analysis performed may be complicated.

Therefore, there exists a need for a surgical instrument that will help healthcare professionals better distinguish tumor tissue from non-tumorous or normal tissue. There also exists a need for a system and/or method capable of addressing the aforementioned problems.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A neurosurgery system for resecting tissue at a surgical site after administration of a contrast agent to a patient is provided. The neurosurgery system includes an electrosurgical instrument for manipulating tissue which generates a fluid sample from the tissue during ablation thereof, an aspiration channel arranged to obtain the fluid sample from the surgical site, and an analyzer for analyzing the fluid sample. The analyzer includes a collector coupled to the aspiration channel and configured to receive at least a portion of the fluid sample from the aspiration channel, a heater configured to atomize the portion of the fluid sample for atomic absorption spectroscopy, and a detector. The detector is configured to measure an absorption of a wavelength corresponding to a rare earth metal of the portion of the fluid sample. The neurosurgery system further includes an indicator configured to provide an indication of a presence of the rare earth metal and a controller disposed in communication with the analyzer and the indicator and configured to control the analyzer and indicator and configured to instruct the indicator to provide the indication of the presence of the rare earth metal based on the measured absorption.

A neurosurgical method for analyzing tissue at a surgical site is provided. The method includes manipulating the tumor tissue at the surgical site with an electrosurgical instrument which generates a fluid sample from the tissue. The method further includes aspirating the fluid sample with an aspiration element including an aspiration channel arranged to obtain the fluid sample, collecting at least a portion of the fluid sample with a collector coupled to the aspiration channel, heating the portion of the fluid sample in the collector with a heater to atomize the portion of the fluid sample, and measuring an absorption of a wavelength corresponding to the rare earth metal with a detector. The method further includes activating, with a controller, an indicator based on the measured absorption to indicate the presence of the rare earth metal.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

Various configurations will be described, by way of example only, and with reference to the accompanying drawings.

DETAILED DESCRIPTION

The present disclosure recognizes the need for a neurosurgical tumor resection system and/or method that provides for elemental analysis of surgical smoke using atomic absorption spectroscopy to distinguish cancerous tissue while in the process of resecting a tumor with an electrosurgical surgical instrument. There also exists a need for a system capable of detecting gadolinium in surgical smoke while in the process of resecting tumor tissue.

For tumor resection surgery, MRI images may be used to show a contrast between tissues to distinguish between healthy tissue and tumor tissue. The contrasts are often subtle. Thus, contrast agents can be introduced to amplify these changes in MRI images. A type of contrast agent is a gadolinium-based contrast agent. Gadolinium is a rare earth element which is not found naturally in biological systems. After being introduced to the body, gadolinium accumulates in tumor tissue. In other words, the contrast agent including a rare earth metal may be used for imaging a target area, including tumor tissue.

Figure 1:
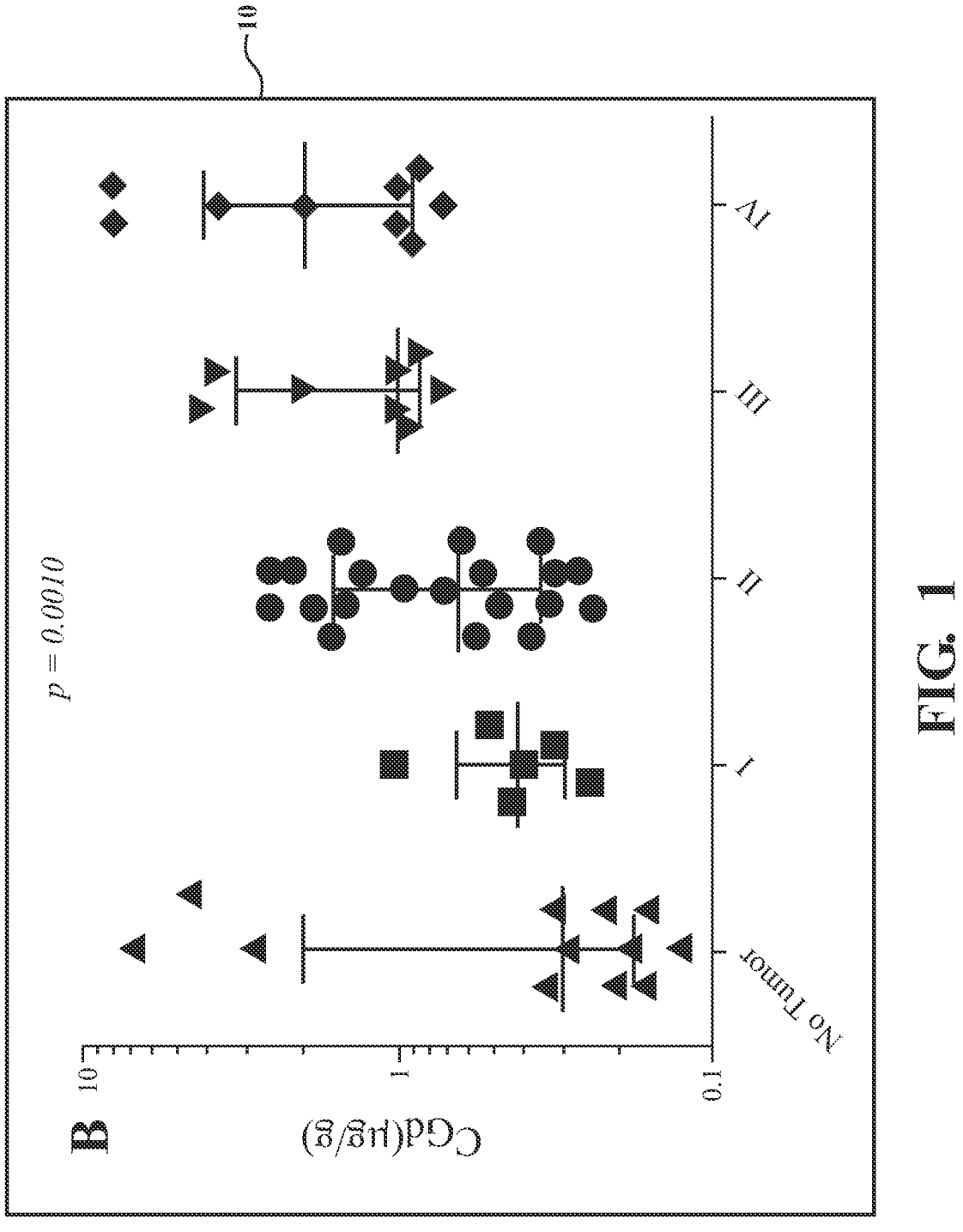
FIG. 1 illustrates concentration levels of gadolinium in different types of tumors, according to the teachings of the present disclosure.

Referring to FIG. 1, chart 10 illustrates concentration levels of gadolinium in different types of tumors. The goal for tumor resection is to achieve gross total resection (GTR), which means there would be no gadolinium-based contrast agent visible in post-operative MRI images. If there is gadolinium-based contrast agent visible in the post-operative MRI images, the healthcare professional did not remove all of the tumor tissue during the surgical procedure, which does not achieve GTR. Thus, a more accurate way of detecting the gadolinium-based contrast agent or different concentration levels of gadolinium in different types of tumors would prove to be beneficial in helping achieve GTR.

Figure 2:
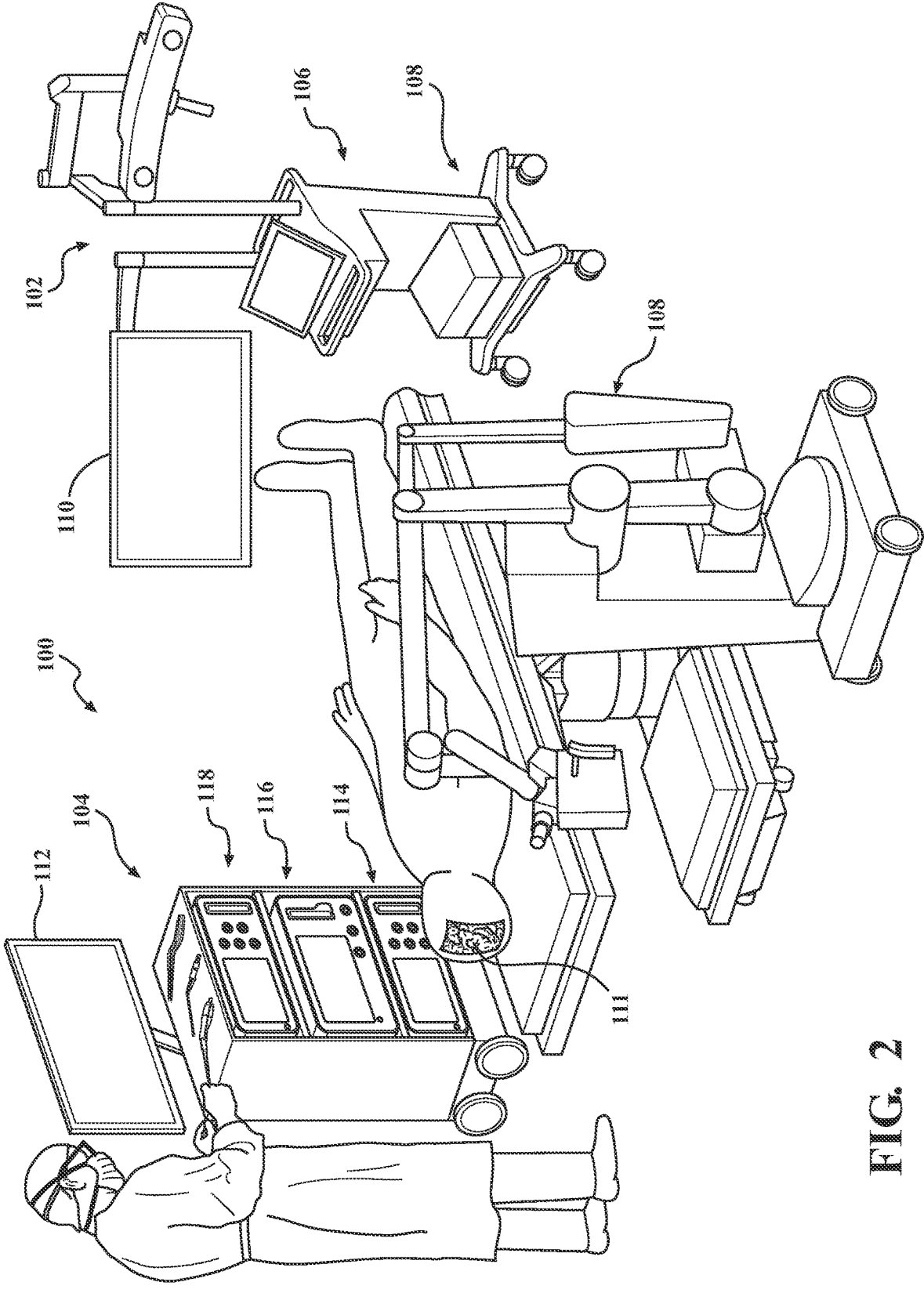
FIG. 2 depicts an example neurosurgery system, according to the teachings of the present disclosure.

Referring to FIG. 2, a neurosurgery system 100 is provided that solves the shortcomings of the prior art. The neurosurgery system 100 may be provided for neurosurgical procedures. Although the disclosure discusses a surgical procedure related to resection of a target tissue of a brain tumor with the administration of a contrast agent including a rare earth metal such as gadolinium, the present disclosure is not limited to tumor resection and may be extended to other types of surgical procedures, to detect other types of tissue, and to detect other types of contrast agents.

The neurosurgery system 100 may include a surgical navigation system 102 and a surgical cart 104. The surgical navigation system 102 includes a cart assembly 106 that houses a navigation computer 108. The navigation computer 108 may also be referred to as the navigation controller. A navigation interface is in operative communication with the navigation computer 108. The navigation interface may include one or more input devices and may be used to input information into the navigation computer 108 or otherwise to select/control certain aspects of the navigation computer 108. The navigation interface includes one or more displays 110. Such input devices may include interactive touchscreen displays/menus, a keyboard, a mouse, a microphone (voice-activation), gesture control devices, or the like.

The tracking system 123 is coupled to the navigation computer 108 and is configured to sense the position of one or more tracking elements attached to a surgical tool or the patient. The tracking system 123 may be configured to track active or passive infrared tracking elements attached to the surgical tool or the patient. An example of a surgical navigation system 102 that may be used is Nav3i™ that is commercially available from Stryker. A surgical navigation system 102 may have various functions and features as described in U.S. Pat. No. 7,725,160 and U.S. Pat. Pub. No. 2020/0100849A1 which are hereby incorporated by reference in their entireties.

A surgical microscope 107 may be used by the healthcare professional to assist in differentiating tumor tissue from non-tumorous or normal tissue. The surgical microscope 107 includes one or more objectives configured to provide magnification in a range (e.g., from about 2 times to about 50 times). The surgical microscope 107 can have a field of view having an area of a predetermined range. The surgical microscope 107 may be configured for microscopy including, but not limited to, fluoresce microscopy and electron microscopy. The surgical microscope 107 may include one or more excitation sources for illuminating and/or visualizing the brain and/or brain tissue 111 during a surgical procedure. The surgical microscope 107 may also include a camera capable of detecting light at different wavelengths.

The navigation computer 108 may be configured to store one or more pre-operative or intra-operative images of the brain. Any suitable imaging device may be used to provide the pre-operative or intra-operative images of the brain. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), and optical coherence tomography (OCT). The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Figures 3A, 3B:
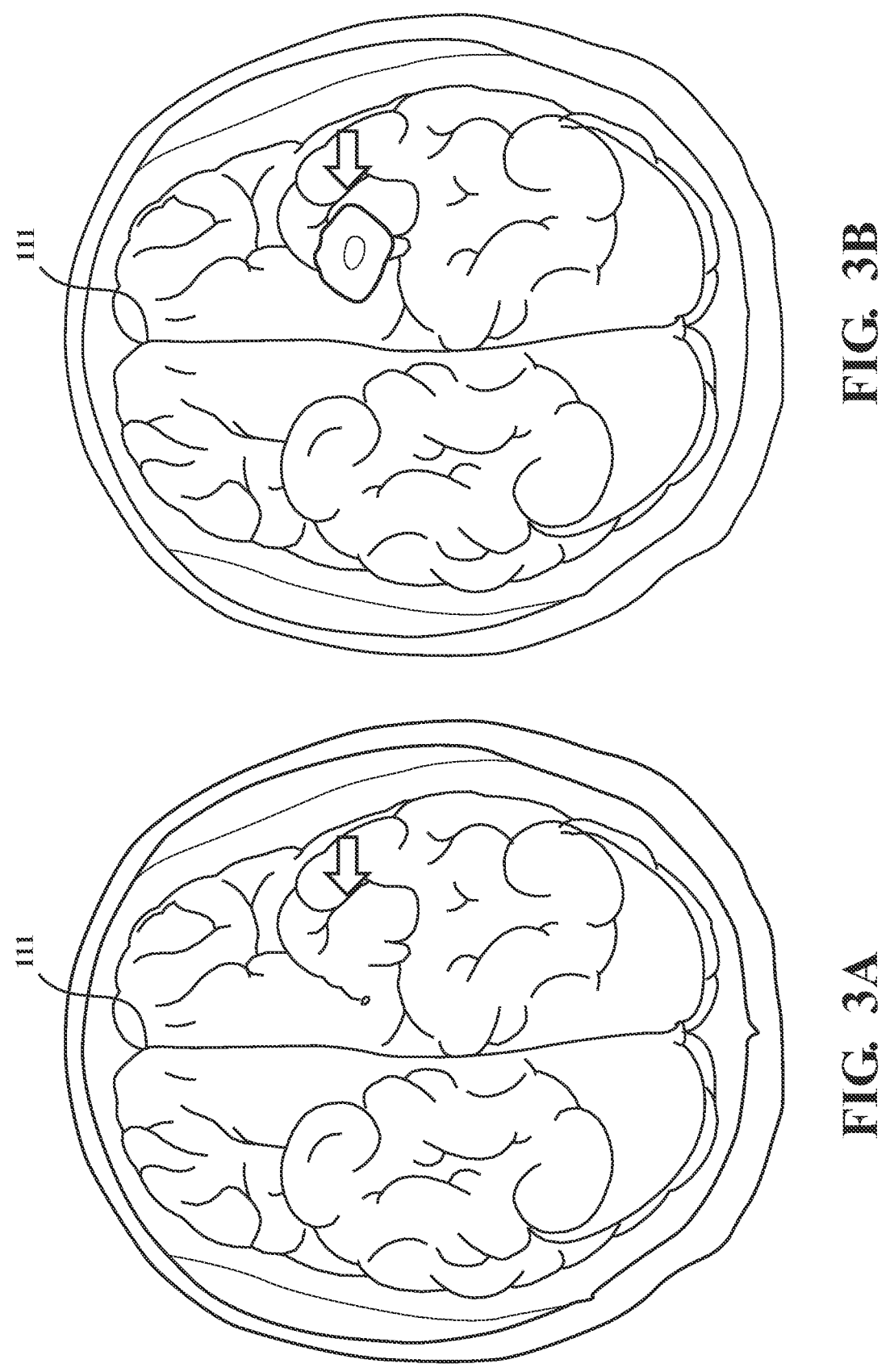
FIGS. 3A and 3B illustrate MRI images of a brain before administration of a contrast agent and after administration of the contrast agent, according to the teachings of the present disclosure.

The navigation computer 108 may generate the one or more images of the brain 111 on a display. For example, the display 110 may show a pre-operative or intra-operative image of the brain 111. Exemplary images of the brain 111 are provided in FIGS. 3A and 3B. With reference to FIGS. 3A and 3B, MRI images of a brain 111 before administration of a contrast agent and after administration of the contrast agent are shown. Before a surgical procedure or while performing a pre-operative routine, a contrast agent may be administered to a patient for acquiring anatomical, physiological, and biochemical information images of a patient's interior. The navigation computer 108 may include more than one display, with one such display showing the pre-operative or intra-operative image of the brain 111, the other display may show a field of view of the surgical site. It is contemplated that the MRI images of FIGS. 3A and 3B may be shown on any other display related to the neurosurgery system 100. Although an MRI image is described, the image data may include MRI image data, x-ray image data, or any other image data obtained by a suitable imaging method known in the art.

The surgical cart 104 may include a surgical system 114, a surgical smoke system 116, and an electrosurgical system 118. A display 112 may be coupled to the surgical cart 104 and operatively connected to the surgical system 114, the surgical smoke system 116, and the electrosurgical system 118 to display information related with each respective system 114, 116, and 118. A healthcare professional may use the electrosurgical system 118 and/or the surgical system 114 to ablate target tissue of the brain 111 of the patient. Different types of ablation are contemplated including, but not limited to, radiofrequency ablation, laser ablation, microwave ablation, and the like.

The electrosurgical system 118 may include an electrosurgical control console 127 and an electrosurgical handpiece assembly 130. The electrosurgical control console 127 may correspond to an ultrasonic control console and the electrosurgical handpiece assembly 130 may correspond to an ultrasonic handpiece assembly 130. The ultrasonic handpiece assembly 130 may comprise an ultrasonic handpiece comprising a proximal end and distal end. The ultrasonic handpiece assembly 130 may further comprise a sleeve and an ultrasonic tip that may be coupled to the distal end of the ultrasonic handpiece. The sleeve may be configured to provide irrigation to the ultrasonic tip and/or the surgical site. It is further contemplated that the sleeve may also be configured to provide aspiration to the ultrasonic tip. The ultrasonic tip may comprise a cutting feature that is configured to ablate, cut, shape, and/or remove biological tissue. The ultrasonic handpiece assembly 130 may have various features, as described in U.S. Pat. Nos. 6,497,715; 6,955, 680; and 6,984,220 and PCT Publication No. WO 2020/ 068756, which are incorporated herein by reference in their entirety.

In another example, the surgical system 114 may correspond to a system that includes bipolar forceps 160 as the surgical instrument. The bipolar forceps 160 may be used by the healthcare professional to grasp, manipulate, and coagulate tissue. The bipolar forceps 160 include an electrode configured to apply current to the tissue. The bipolar forceps 160 are adapted to generate fluid samples from the surgical site by contacting the tissue with the electrode. The bipolar forceps 160 may have features, as described in U.S. Pat. No. 8,361,070, which is hereby incorporated by reference in its entirety.

While the disclosure discusses and illustrates that the surgical instrument may include a suction tool and bipolar forceps 160, the surgical system 114 and surgical instrument may include other tools. In another example, the surgical instrument may include a neuro stimulator, a dissector, or an ablation device (e.g., an RF ablation device and/or a laser ablation device). It is contemplated that the surgical instrument may be any type of electrosurgical instrument. For example, the surgical instrument may be an electrosurgical instrument that may be adapted for laser ablation. Any number of surgical systems and any number of surgical instruments may be employed by the healthcare professional in performing the surgical procedure.

The surgical system 114 may include a surgical instrument and a surgical control console 115 to control various aspects of the surgical instrument. The healthcare professional may also use the surgical instrument to perform any surgical operation on the tissue. For example, to ablate the tissue, to suction fluid or debris from the tissue, to cauterize the tissue, or combinations thereof. In an example, the surgical system 114 may correspond to a suction system in which the surgical instrument corresponds to a suction tool for removing fluid and/or debris from the surgical site. The suction system may have various features, as described in as described in U.S. Pat. No. 9,066,658 and U.S. Pat. Pub. No. 20180344993 which are hereby incorporated herein by reference in their entireties. While the disclosure contemplates bipolar forceps 160 and the suction tool as the surgical instrument, it is understood that the surgical system 114 may correspond to any surgical system 114 and include any number of surgical instruments.

Figure 4:
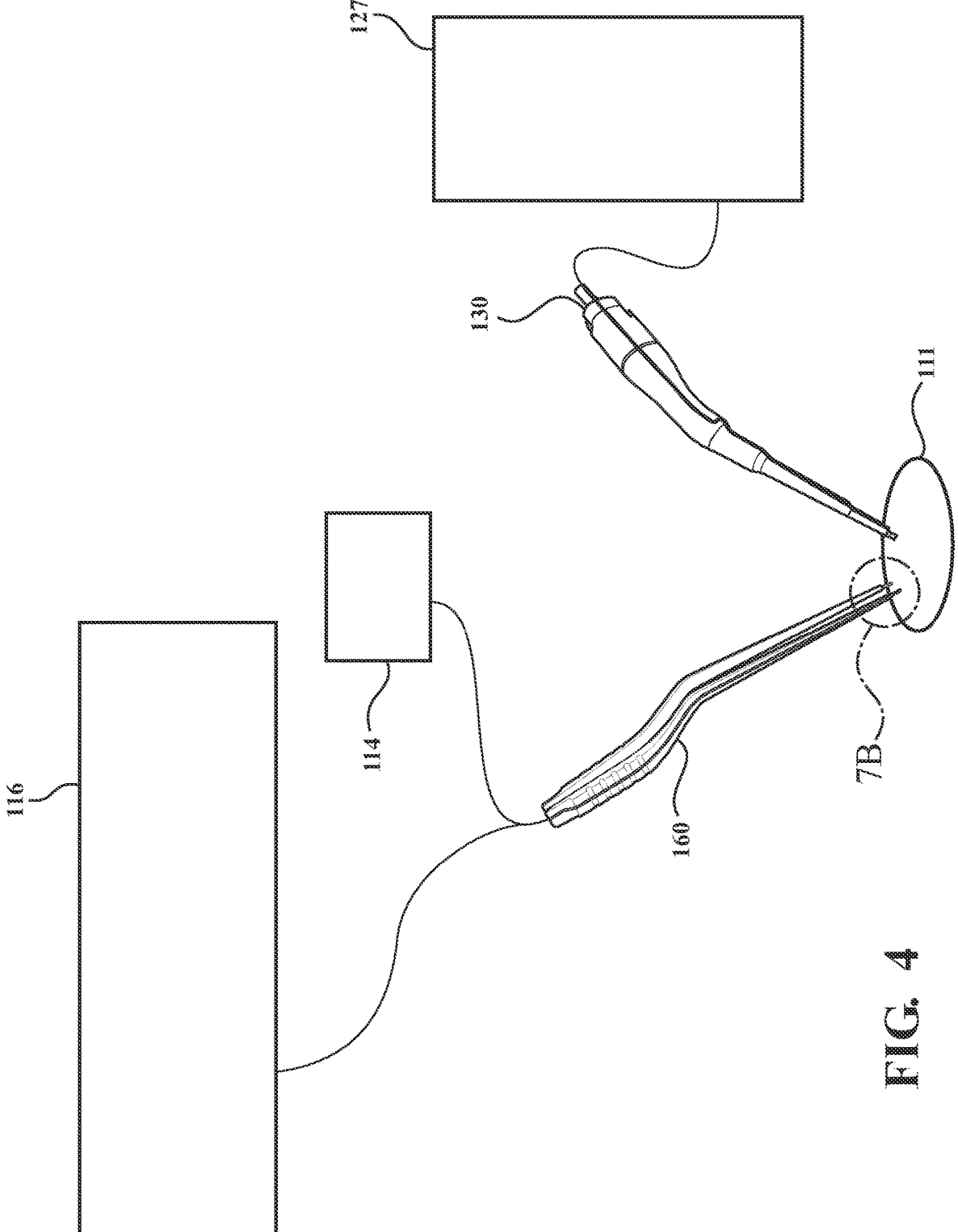
FIG. 4 depicts a functional block diagram of a neurosurgery system, according to the teachings of the present disclosure.

With reference to FIG. 4, a functional block diagram of the neurosurgery system 100 is provided. The surgical smoke system 116 may be used in conjunction with any number of surgical systems and/or surgical instruments. For example, as shown in FIG. 3, the surgical smoke system 116 is being used with a surgical system that includes the bipolar forceps 160. It is contemplated that the surgical instrument may be any type of surgical instrument.

The bipolar forceps 160 are adapted to generate the fluid sample from the surgical site by contacting the tissue. The healthcare professional may manipulate the tissue with the bipolar forceps 160, which generates surgical smoke or a fluid sample from the tissue. For example, during tissue ablation, contacting tissue with the bipolar forceps 160 can cause the tissue to heat up and vaporize thereby generating surgical smoke or a fluid sample including, but not limited to, aerosol, vapor, and fume. In other words, the bipolar forceps 160 may apply thermal energy to tissue in order to generate surgical smoke or a fluid sample. During ablation, electricity with rapidly alternating polarity is passed from an electrode, through tissue, and back to the ground. At these high frequencies, where the current density is at the highest, there is resistive heating of the tissue. When tissue temperature reaches at least 55 degrees Celsius, cells in the vicinity die. If more energy is applied, the temperature keeps rising, and the dead cells become desiccated, and the proteins coagulate. If yet more energy is applied, heat rises, and the tissue will be vaporized, generating the fluid sample. The present disclosure provides for the analysis of the fluid sample to aid the healthcare professional during a surgical procedure.

Current surgical methods rely on the healthcare professional's ability to differentiate tumor tissue from non-tumorous or normal tissue using their trained eyes and sometimes with the help of an operating microscope and/or diagnostic imaging from scans performed before surgery to remove the tumor tissue. Particularly, MRI images may be used to show a contrast between tissues to distinguish between normal tissue and tumor tissue. However, the contrast may be subtle or certain diseases remain undetectable by MRI. Thus, referencing back to FIGS. 3A and 3B, contrast agents may be introduced to amplify these changes in MRI images. A particular type of contrast agent is a gadolinium-based contrast agent. Gadolinium is a rare-earth element which is not found naturally in biological systems and after being introduced to the body, gadolinium accumulates in tumor tissue. Gadolinium may allow for visualization of tumors in an MRI image by enhancing the quality of the image and allowing healthcare professionals to more accurately and efficiently perform surgical procedures. It is contemplated that any type of gadolinium-based contrast agent is applicable, including, but not limited to, gadopentetate dimeglumine (gadolinium diethylene triamine pentaacetic acid (Gd-DTPA), gadodiamide (gadolinium diethylene triamine penta-acetic acid bis-methylamide (GD-DTPA-BMA), Gadoteridol (Gadolinium-1,4,7-tris (carboxymethyl)-10-(2' hydroxypropyl)-1, 4, 7-10-tetraazacyclododecane (Gd-HPD03A]), gadoterate meglumine (gadolinium-tetraazacyclododecane tetra acetic acid (Gd-DOTA), Dotarem®, gadobenate dimeglumine, or gadobutrol.

Based on the image data in conjunction with a contrast agent, the healthcare professional may preoperatively plan a surgical strategy to resect a target tissue of a brain tumor. However, during surgery, the healthcare professional may still have to rely on their own ability to sense the subtle changes in color, texture, and/or mechanical properties to identify which tissue should be removed. The present disclosure provides for analysis of the surgical smoke to aid the healthcare professional during the surgical procedure in identifying the target tissue or the brain tumor.

Figure 5:
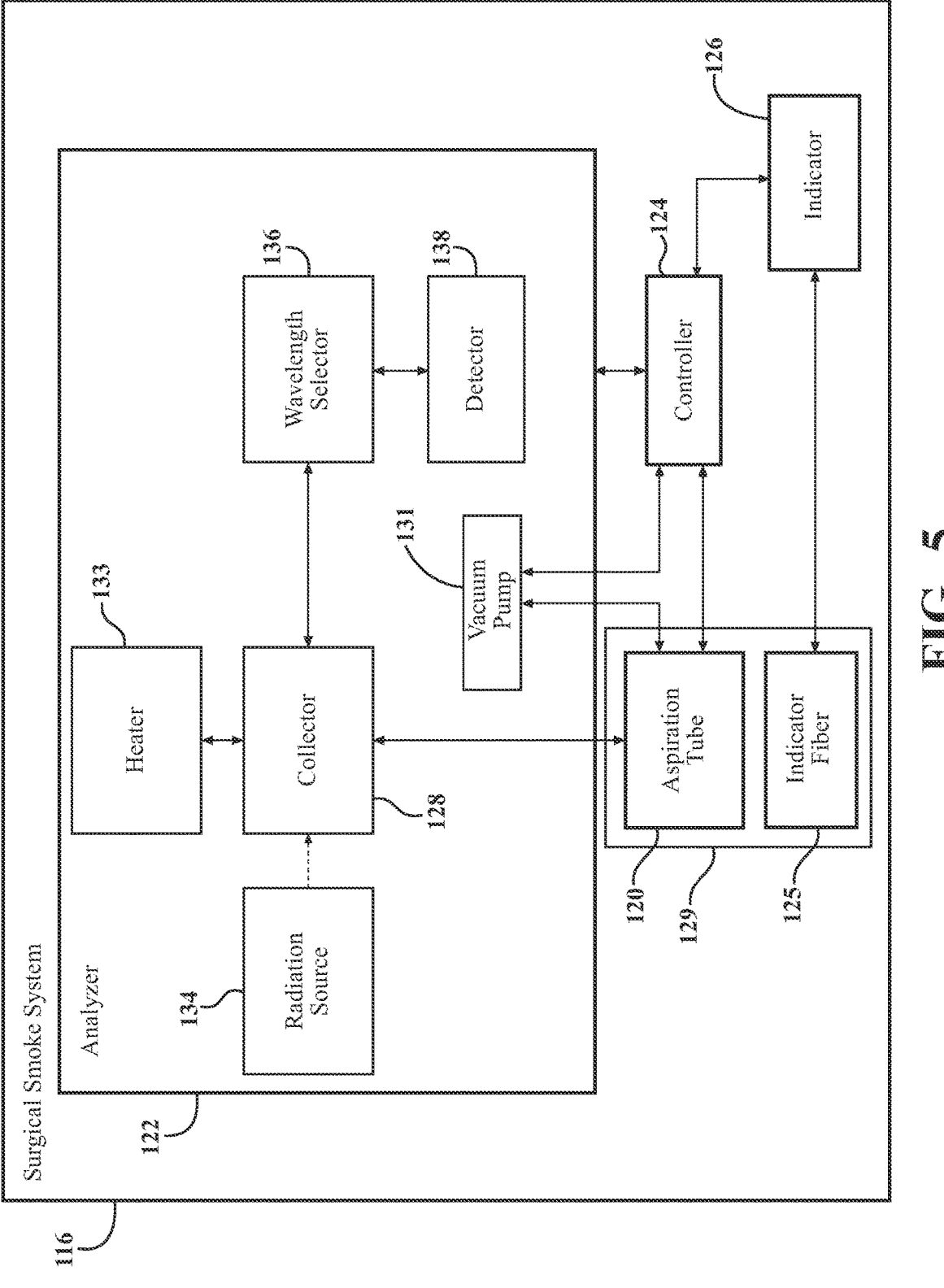
FIG. 5 depicts a functional block diagram of a surgical smoke system of a neurosurgery system, according to the teachings of the present disclosure.

Referring to FIG. 5, a functional block diagram of the surgical smoke system 116 is depicted. The surgical smoke system 116 includes an aspiration element 129 arranged to obtain the fluid sample(s) from a surgical site, an analyzer 122 for analyzing the fluid sample, a controller 124 configured to determine a concentration of a rare earth metal in the fluid sample, and an indicator 126.

The analyzer 122 includes a collector 128 coupled to the aspiration element 129, a heater 133, a wavelength selector 136, a detector 138, and, optionally, a radiation source 134. In some configurations, the analyzer 122 may be realized as an atomic absorption spectroscopy device. The wavelength selector 136 is configured to receive the light passed through the collector 128 and heater 133 and the detector 138 is coupled to the wavelength selector 136. Each component will be discussed in greater detail below.

The present disclosure provides for a system and/or method for elemental analysis of the fluid sample(s) to distinguish cancerous tissue while in the process of resecting a tumor with a surgical instrument. It is contemplated that samples collected from the surgical site may include any type of fluid samples and/or solid samples. Particularly, the surgical smoke system 116, including the analyzer 122, provides for gadolinium detection in fluid samples using atomic absorption spectroscopy while in the process of resecting a tumor. The analysis of fluid samples during the surgical procedure may be performed using atomic absorption spectrometry (AAS) to provide elemental analysis of fluid samples. AAS detects elements in samples through the application of characteristic wavelengths of electromagnetic radiation.

As an overview, AAS determines the concentration of a substance or rare earth metal by the reduction in intensity of light due to light absorbed by atomized atoms of the rare earth metal at the atomic absorption wavelength(s) specific for that rare earth metal. The rare earth metal is atomized into an elemental form using heat. Any type of atomizers are contemplated. For instance, the fluid sample may be nebulized into a flame, provided by the heater 133, which atomizes the rare earth metal. A radiation source 134 is aimed at the flame. The analyzer 122 is configured to enable atomic absorption spectroscopy by measuring an absorption of a wavelength corresponding to a rare earth metal. More specifically, an absorption signal (reduction in light intensity due to absorption of light by the atoms causing a transition in the atoms to an excited state) is measured by the detector 138 at a wavelength corresponding to the rare earth metal.

The wavelength selector 136, such as a monochromator, may be positioned between the heater 133 and the detector 138 to pass only light corresponding to or characteristic for the rare earth metal. Gadolinium, a rare earth metal, concentrations can thus be determined via comparison to calibration curves based on measured absorption for known concentrations. Although the present disclosure discusses the rare earth metal as being gadolinium, it is contemplated that other types of rare earth metal are applicable. Components and functions of the analyzer 122 will be discussed in greater detail below.

Other types of elemental analysis techniques are contemplated. For example, the analysis may be performed using atomic emission spectrometry. The determination of the concentration of a substance is accomplished by using the measurement of the intensity of emitted light at wavelengths specific for excited atoms of the substance. In another example, the analysis may be performed using atomic fluorescence spectrometry. The determination of the concentration of a substance is accomplished by using the measurement of the intensity of fluorescent light at wavelengths specific for excited atoms of the substance.

Figure 6:
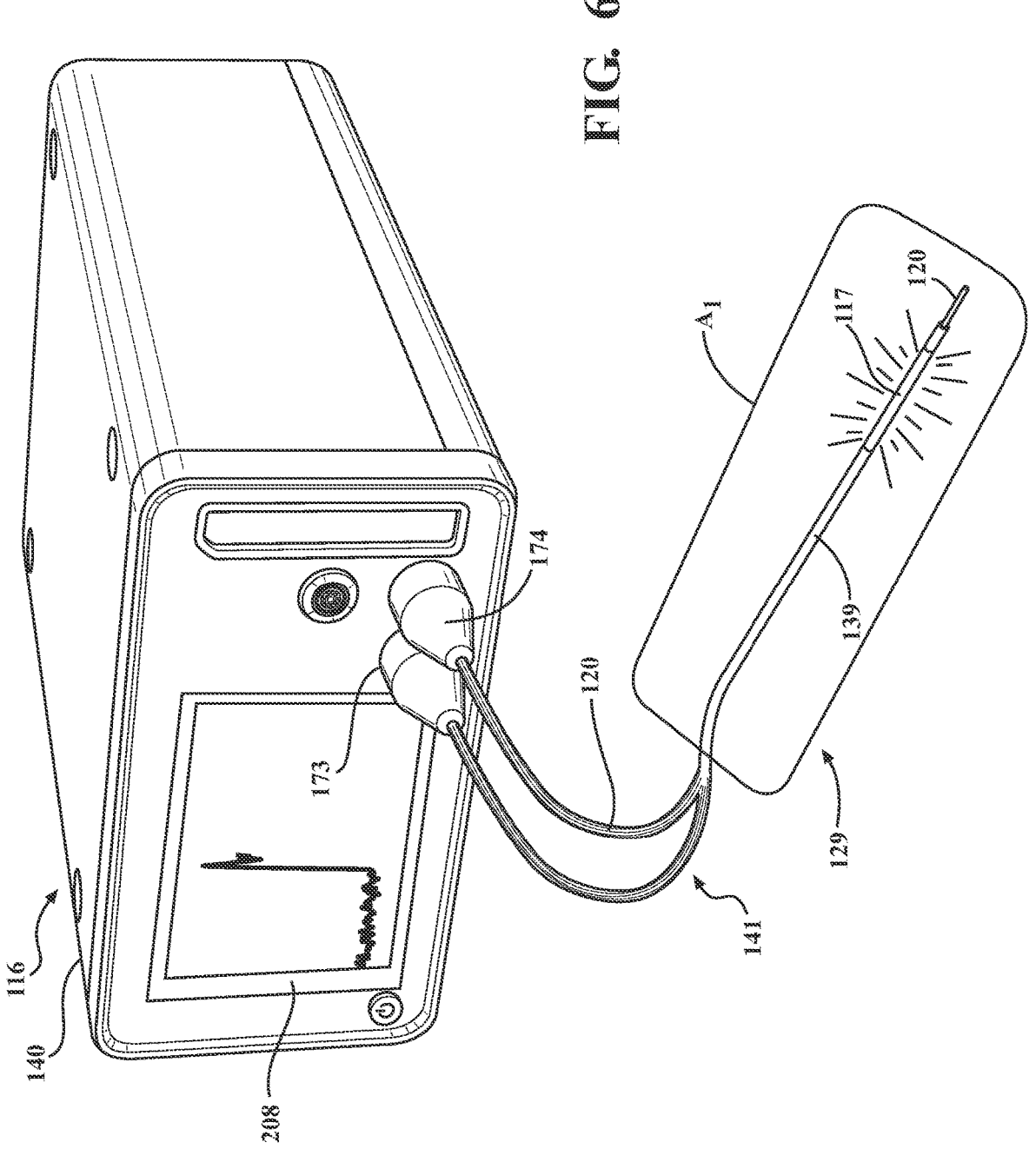
FIG. 6 illustrates an exemplary surgical smoke system of a neurosurgery system.

Referring to FIG. 6, an exemplary surgical smoke system 116 including an aspiration element 129 is provided. The aspiration element 129 may include a tubular structure 139, an aspiration channel 120, and an indicator fiber 141. The tubular structure 139 may be formed to include a central portion and an outer channel. The aspiration element 129 may comprise a proximal end and distal end with the aspiration channel 120 extending at least partially from the proximal end to the distal end or vice versa. In some configurations, an aspiration tube may define the aspiration channel 120 and the aspiration channel 120 may be disposed within the central portion while the indicator fiber 141 is disposed within the outer channel. A proximal end of the aspiration channel 120 may extend past a proximal portion of the tubular structure 139.

The indicator fiber 141 may be optically coupled to the indicator 126 which may generate visible light from any suitable wavelength of the visible light spectrum when activated by the controller. For example, the indicator may generate green light (e.g., wavelengths of about 520-564 nm) when instructed by the controller 124 to indicate the detection of the target tissue. While the indicator fiber 141 and any other fibers discussed herein as single fibers for simplicity, it is understood that each of the fibers may include one or more fiber. It is contemplated that the indicator fiber 141 may include any number of fibers. The indicator may include any type of light source sources such as a light emitting diode (LED), a laser diode, a pulsed laser, a continuous wave laser, and a modulated laser. The tubular structure 139 may include an indication section 117. The indication section 117 may correspond to a transparent portion of the tubular structure 139 or a removed portion of the tubular structure 139. For example, the removed portion of the tubular structure 139 may expose at least a portion of the outer channel so that the indicator fiber 141 is visible. The indication section 117 allows for a healthcare professional to view the light traveling down the indicator fiber 141.

In some configurations, the indicator may be realized as a light emitting diode (LED). The LED may be disposed on the aspiration element 129 or the aspiration channel 120 proximally to the distal end of the aspiration element 129 or the aspiration channel 120. The indicator may be configured to emit light in response to detection of tumorous or target tissue. The indicator may be any shape, including, but not limited to, sphere shaped, dome shaped, cylinder shaped, or another suitable shape. As such with this configuration, the indicator fiber 141 and the indicator 126 within the control console 140 may be omitted.

The surgical smoke system 116 may include a control console 140 to provide the healthcare professional with a real-time indication when gadolinium is detected. The control console 140 may include the controller 124, the analyzer 122, a user interface 208, a vacuum pump 131, and/or the indicator 126. The user interface 208 may include a display for displaying output from the controller 124. The control console 140 may further include an indicator port 173 and an aspiration port 174. The indicator port 173 may connect the indicator fiber 141 to the control console 140. The aspiration port 174 may connect the aspiration channel 120 to the control console 140 as shown in FIG. 6.

The aspiration element 129 including the aspiration channel 120 may be associated with evacuation and/or with infusion of samples from and to a surgical site when using an electrosurgical instrument. More specifically, the aspiration channel 120 is arranged to obtain fluid samples from the surgical site for analysis. It is contemplated that samples collected from the surgical site may include any type of gas samples, liquid samples, and/or solid samples. Further, the aspiration channel 120 may allow for removal of ablated tissue and/or fluid sample from the surgical site when a vacuum is applied. As will be discussed in greater detail below, the surgical smoke system 116 determines the presence or absence of tumor tissue based on the concentration of gadolinium in the portion of the fluid sample collected from the surgical site during tumor resection.

The aspiration channel 120 may be connected to an aspiration line of the surgical smoke system 116. The vacuum pump 131 may be coupled to the aspiration channel 120 via the aspiration line. It is contemplated that the aspiration channel 120 may be connected to any aspiration line or vacuum source directly or indirectly. For example, as mentioned above, the aspiration channel 120 may be connected, directly or indirectly, to an aspiration line of the electrical surgical instrument. The aspiration channel 120 may be connected, directly or indirectly, to a wall suction port (i.e., vacuum outlet) of a medical facility, a portable suction system, or another control console that includes a vacuum source. It is also contemplated that the analyzer 122 or any other component of the surgical smoke system 116 may include the vacuum pump 131.

Figure 7A:
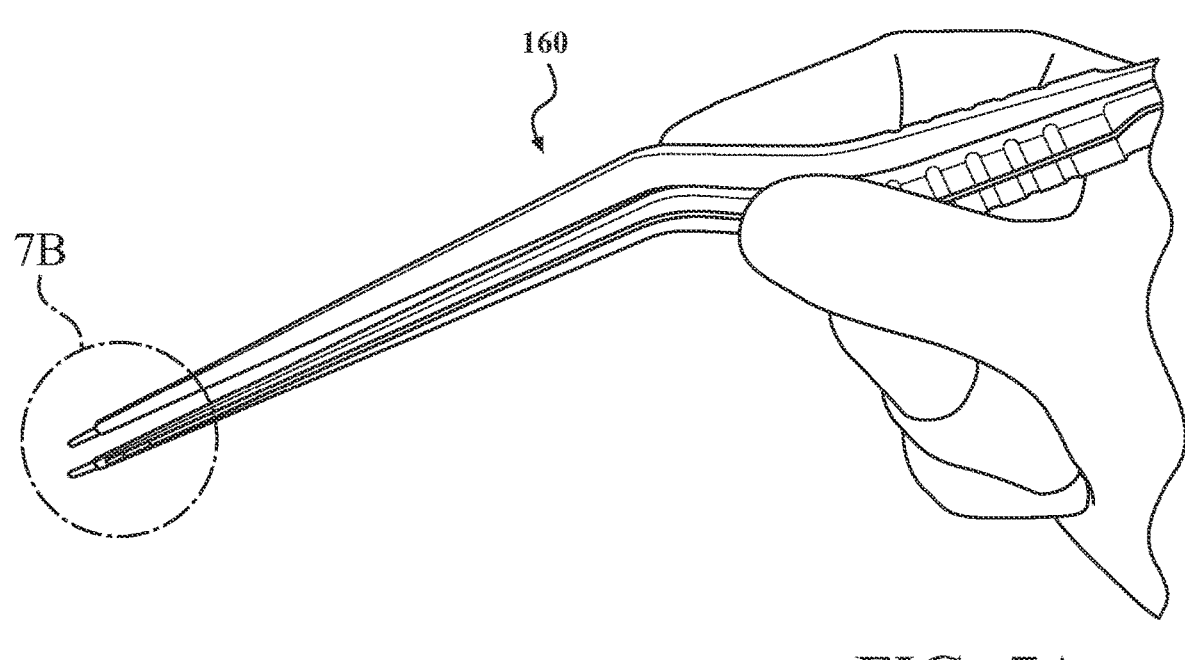
FIGS. 7A and 7B illustrate an aspiration element coupled to a surgical instrument of the neurosurgery system, according to the teachings of the present disclosure.
Figure 7B:
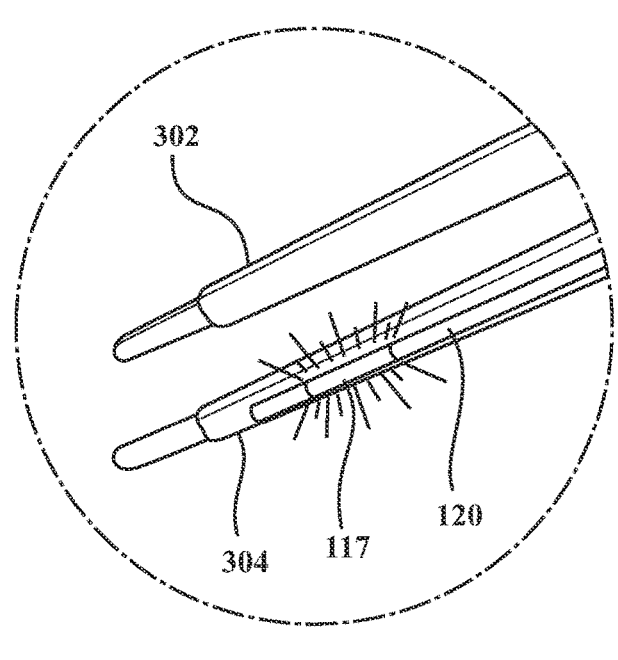
Figure 8A:
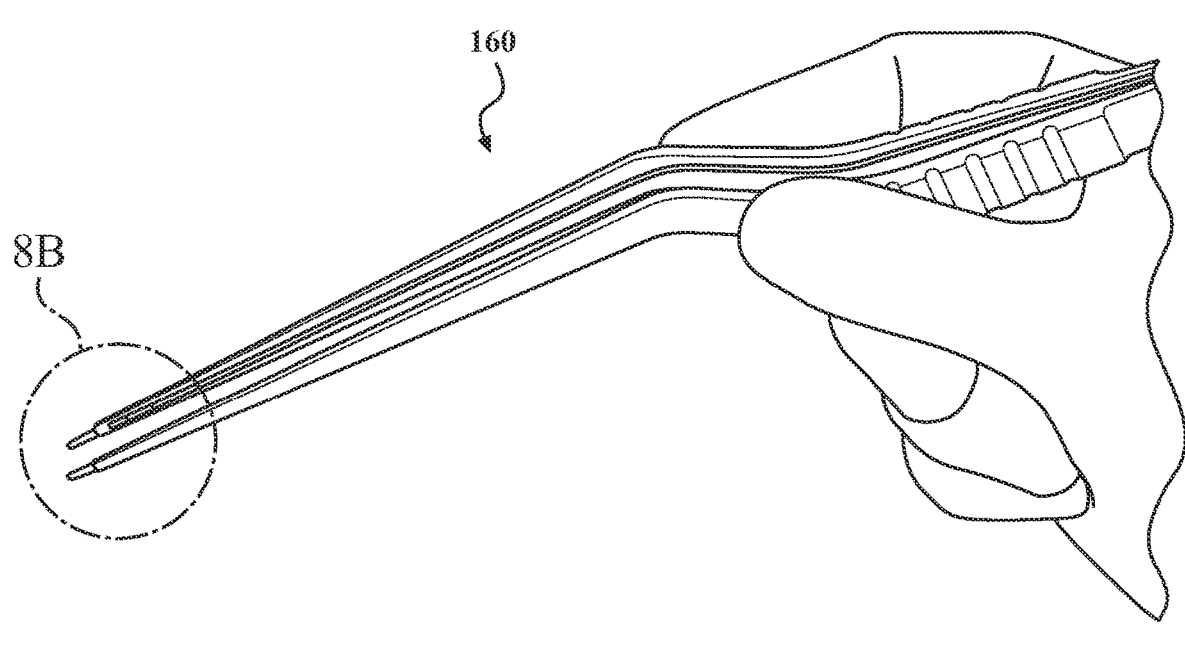
FIGS. 8A and 8B illustrate an aspiration element coupled to a surgical instrument of the neurosurgery system, according to another configuration.
Figure 8B:
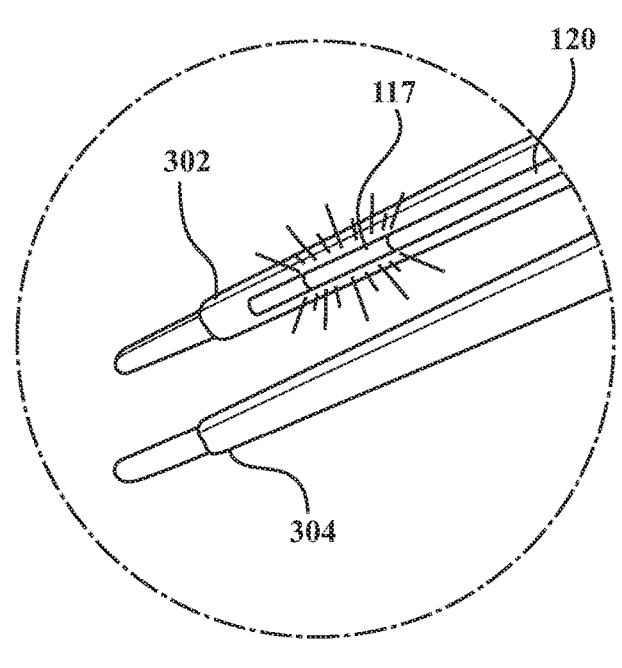
Figure 9A:
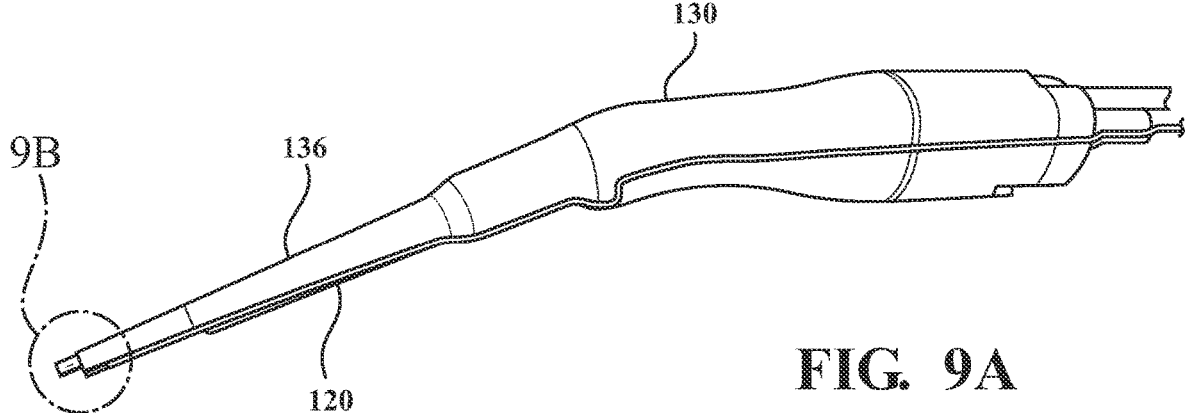
FIGS. 9A and 9B illustrate an aspiration element coupled to a surgical instrument of the neurosurgery system, according to the teachings of the present disclosure.
Figure 9B:
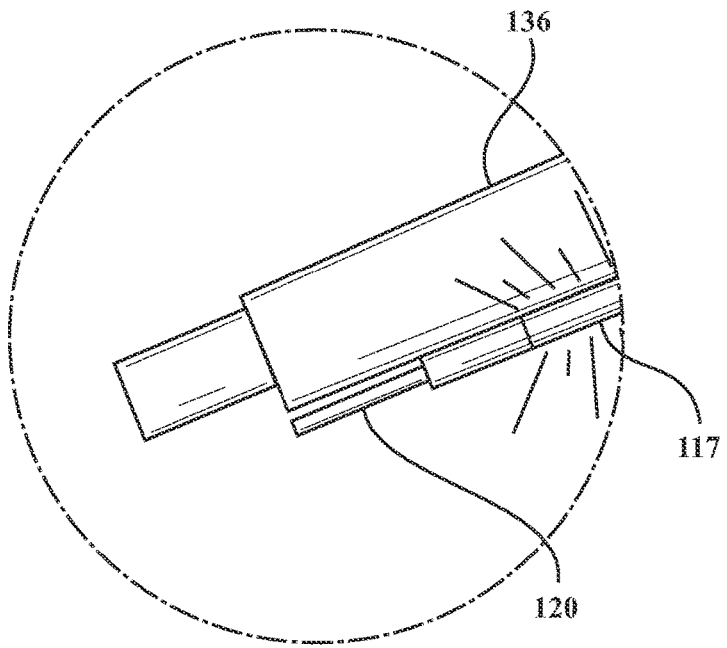

With reference to FIGS. 7A-9B, the aspiration element 129 (or the aspiration channel 120 and the indicator fiber 141) may couple to any surgical or electrosurgical instrument. For example, the aspiration element 129 may be coupled to the bipolar forceps 160 (or any surgical tool associated with the system 100 such as dissector, etc.) as shown in FIGS. 7A-8B or the ultrasonic handpiece assembly 130, as shown in FIGS. 9A and 9B. The aspiration element 129, including the aspiration channel 120, may be coupled to the surgical instrument in any suitable manner.

The aspiration element 129 (or the aspiration channel 120 and/or indicator 126) may be integrally formed with the surgical instrument. It is contemplated that the aspiration channel 120 may be integral to or otherwise functionally associated with the surgical instrument. It is also contemplated that the aspiration element 129 (or the aspiration channel 120 and/or indicator 126) may be completely or at least partially integral to the electrosurgical instrument. In another example, the aspiration element 129 (or the aspiration channel 120 and/or indicator 126) may be a separate component configured to couple to the surgical instrument.

For instance, the aspiration element 129 (or the aspiration channel 120 and/or indicator 126) may be coupled the surgical instrument via an adhesive. The adhesive may be in the form of a sticker or substance such as glue. Additionally or alternatively, the aspiration element 129 (or the aspiration channel 120 and/or indicator 126) may also be coupled to the surgical instrument via a fixation element. The fixation element may include a clip, a band, or anything that may secure the aspiration element 129 (or the aspiration channel 120 and/or indicator 126) to the surgical instrument.

With reference to FIGS. 7A-8B, the bipolar forceps 160 may include a pair of pincers, more specifically, a first pincer 302 and a second pincer 304. The aspiration element 129 (or the aspiration channel 120 and/or an indicator) may be coupled to any portion of the bipolar forceps 160. For instance, as shown in FIGS. 7A-7B, the aspiration channel 120 extends along an outer portion of the second pincer 304 of the bipolar forceps 160. In another configuration, as shown in FIGS. 8A-8B, the aspiration channel 120 extends along an inner portion of the first pincer 302.

In the configurations shown in FIGS. 7B and 8B, the indication section 117 is disposed near the tip of the second pincer 304 and the first pincer 302, respectively, such that the healthcare professional can view light emitted via the indication section 117 while performing resection of the target tissue without having to break eye contact with the sterile field. It is contemplated that the indication section 117 may be disposed in any suitable location relative to the first or second pincers 302, 304.

As shown in FIGS. 9A and 9B, the aspiration element 129 may be coupled to the ultrasonic handpiece assembly 130. The ultrasonic handpiece assembly 130 or any other surgical instrument may comprise a proximal end and a distal end. The aspiration element 129 is configured to be disposed proximally to the distal end of the surgical instrument. The aspiration channel 120 may be coupled to the ultrasonic handpiece assembly 130 in any manner as long as there is no direct contact between the tip and the aspiration channel 120. For example, the aspiration channel 120 may terminate at a portion of the sleeve proximal to the tip. In another example, the aspiration channel 120 may extend past the sleeve but be arranged such that there is adequate empty space between the tip and the sample element 164 to prevent contact between the tip and the sample element 164. In some configurations, the aspiration channel 120 may be integrated with a portion of the sleeve.

The aspiration channel 120 may define a lumen through the aspiration channel body. The aspiration channel 120 may define any number of lumens to provide at least one aspiration passageway. It is contemplated that the aspiration channel 120 may be integrated with a surgical instrument. For example, the ultrasonic handpiece assembly 130 may comprise the aspiration channel 120. The aspiration channel 120 may at least partially be disposed within the ultrasonic handpiece and configured to define a first lumen through the ultrasonic handpiece for suction. In such configurations, the aspiration channel 120 may couple to an aspiration line of the surgical smoke system 116.

Further, in some configurations, the indicator 126 may be realized as one or more LED(s) or another form of light source coupled to the ultrasonic handpiece and configured to emit light when the presence of gadolinium in the fluid sample is detected thereby indicating a tumorous tissue.

The aspiration channel 120 may define an additional lumen through the ultrasonic handpiece to the passageway defined by the lumen of a transducer and a second conduit of the horn. For example, the aspiration channel 120 may define an irrigation lumen through the ultrasonic handpiece and the first lumen through the transducer and the second conduit through horn may define an aspiration lumen through the ultrasonic handpiece. Alternatively, the aspiration channel 120 may define an aspiration passageway through the ultrasonic handpiece and the first lumen through the transducer and the second conduit through the horn may define an irrigation passageway through the ultrasonic handpiece. Alternatively, the aspiration channel 120 may define two aspiration passageways with one aspiration passageway through the ultrasonic handpiece and the first lumen through the transducer and the second conduit through the horn may define the second aspiration passageway through the ultrasonic handpiece.

The aspiration channel 120 is arranged to transport the fluid sample from the surgical site to the analyzer 122 for atomic absorption spectroscopy. Specifically, the collector 128 couples to the aspiration channel 120 and is configured to receive at least a portion of the fluid sample from the aspiration channel 120. Once the fluid sample is obtained in the collector 128, the heater 133 volatizes and atomizes the portion of the fluid sample. The heater 133 is configured to couple to the collector 128 and may be positioned relative to the collector 128. For example, the heater 133 may be positioned below the collector 128. The heater 133 emits a flame or heat towards the fluid sample in the collector 128 to desolvate, volatize, and atomize the fluid sample into an elemental form. The radiation source 134 includes a light source, such as a hollow cathode lamp, that emits light with a bright-line spectrum. The radiation source 134 reaches the collector 128 and the flame. The radiation source 134 is arranged along the collector 128 and is orientated to emit light towards the portion of the fluid sample in the collector 128.

When the light from the radiation source 134 reaches the flame, a light component at a specific wavelength is absorbed in a composition contained in the fluid sample inside the flame. The light from which the light component at the specific wavelength has been absorbed in this manner passes through to the wavelength selector 136 and the detector 138.

As discuss previously, the wavelength selector 136 may be a monochromator and may be positioned between the heater 133 and the detector 138. The wavelength selector 136 may be configured to isolate the specific wavelength corresponding to a particular substance. The wavelength selector 136 serves to select a specific wavelength of light which is absorbed by the sample, and excludes other wavelengths. The selection of the specific wavelength allows the determination of a selected element in the presence of others. For example, the wavelength selector 136 may isolate the wavelength corresponding to gadolinium. A specific substance, such as gadolinium, can be identified and measured by measuring the intensity of the specific wavelength light because the specific wavelength light is absorbed by electron excitement resulting from the unique potential difference of the specific type of atom. Once the wavelength selector 136 selects a wavelength corresponding to gadolinium, the wavelength selector 136 outputs the wavelength to the detector 138.

The detector 138 may be configured to receive the outputted wavelength from the wavelength selector 136. The detector 138 is configured to detect the wavelength corresponding to the rare earth metal or gadolinium, measure an absorption of the wavelength to determine the concentration of gadolinium, and transmit a signal representative of the measured absorption of the wavelength, and/or concentration of gadolinium. The detector 138 may enable detection and analysis of the rare earth metal or gadolinium. More specifically, the detector 138 may be configured to convert the optical signals received from the wavelength selector 136 into spectral signals in the form of electrical signals and transmit the signals which are representative of the absorption of the wavelength corresponding to gadolinium to the controller 124 of the surgical smoke system 116.

Based on transmitted signal from the detector 138 to the controller 124, the controller 124 may be configured to compare the measured absorption to a calibration curve which represents a relationship between concentration and absorbance of gadolinium in order to determine the concentration of gadolinium. In some configurations, the controller 124 may store a predetermined concentration threshold which has been associated with tumor tissue and gadolinium. Based on the concentration of the gadolinium, the controller 124 may generate an indication signal to control the indicator 126. In other words, based on the concentration of the rare earth metal and/or comparison to the concentration threshold, the indicator 126 may be activated, thereby providing an indication via the indication section to the healthcare professional, during surgery, of the presence of the gadolinium in the fluid sample which is evidence of tumorous tissue.

The controller 124 may control operation of the indicator 126. The controller 124 may activate the indicator 126 to emit light to indicate the presence of the rare earth metal if the fluid sample indicates a tumorous tissue. The controller 124 may be configured to control (e.g., deactivate) the indicator 126 in response to the absence of the rare earth metal in the fluid sample to convey that the tissue is non-tumorous. The indicator 126 may also be an LED or another form of light source coupled to the electrosurgical instrument and configured to emit light when the presence of gadolinium in the fluid sample is detected, thereby indicating a tumorous tissue. In another example, the indicator 126 may be configured to emit another light in the absence of gadolinium thereby indicating a non-tumorous tissue. It is contemplated that the surgical smoke system may provide another type of indication including, but not limited to, audio, visual, tactile, haptic and the like.

Figure 10:
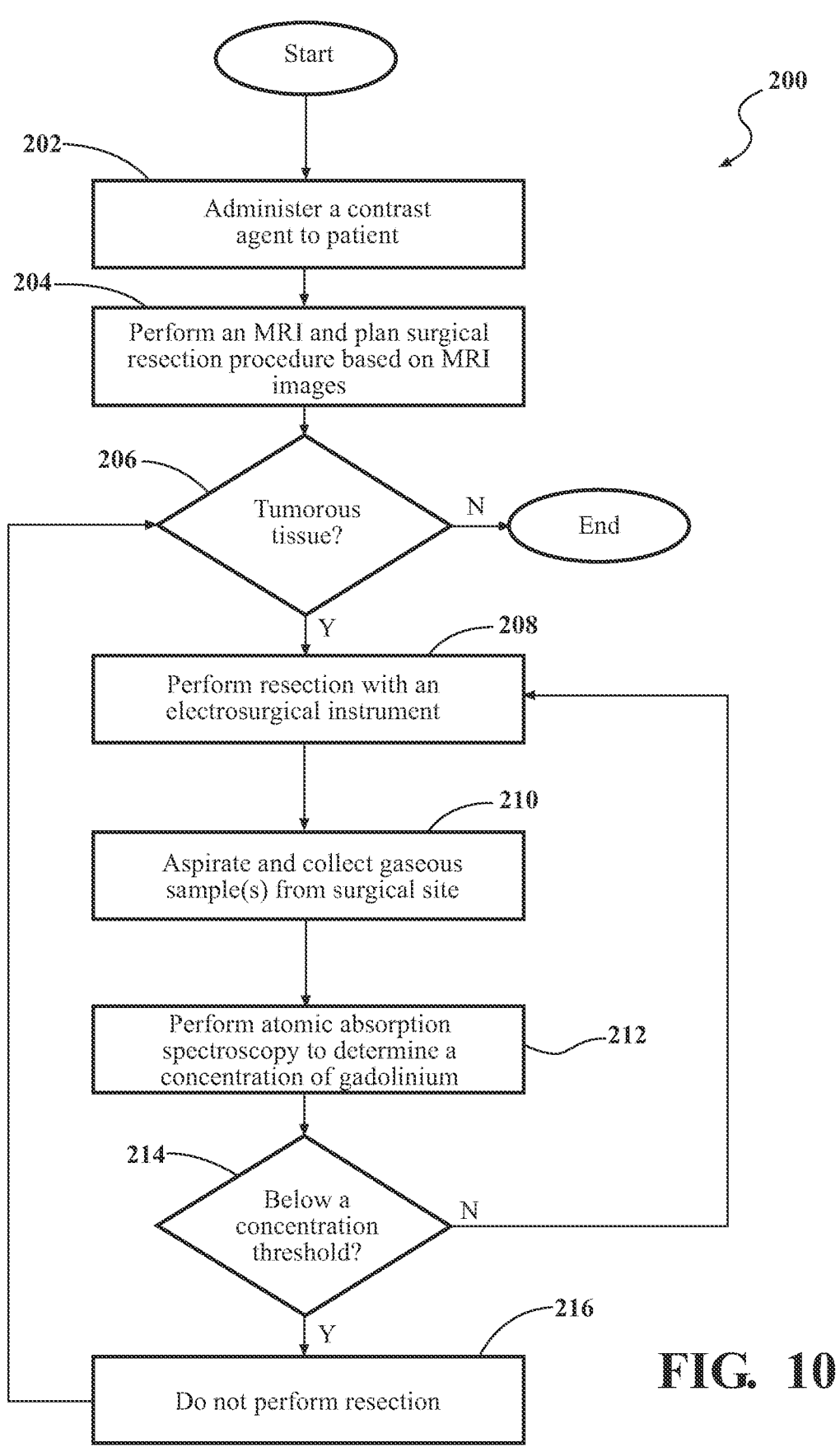
FIG. 10 illustrates an exemplary surgical resection procedure performed with an electrosurgical smoke system, according to the teachings of the present disclosure.

Referring to FIG. 10, a flow chart 200 illustrating tumor resection in accordance with the present disclosure is provided. As will be appreciated from the subsequent description below, this flowchart merely represents an exemplary and non-limiting sequence of blocks to describe a typical resection procedure performed to resect target tissue and is in no way intended to serve as a complete functional block diagram of all of the steps of a resection procedure.

The flow chart 200 begins at 202 where a contrast agent is administered to a patient as part of performing a pre-operative routine. The contrast agent is a gadolinium-based contrast agent. At 204, after the gadolinium-based contrast agent is administered, an MRI is performed and the healthcare professional may plan the surgical procedure, such as a tumor resection, based on the MRI images. At 206, the healthcare professional determines whether there is tumor tissue based on the MRI images. If there is no tumor tissue present, the resection procedure may end, otherwise, the resection procedure continues to 208.

At 208, the healthcare professional may perform resection of the tumor tissue using one of the abovementioned electrosurgical instruments. The tissue is manipulated with the electrosurgical instrument which generates surgical smoke or a fluid sample from the tissue. At 210, the fluid sample is aspirated and collected from the surgical site. At 212, atomic absorption spectroscopy is performed by the surgical smoke system 116 as mentioned above. The surgical smoke system 116 determines a concentration of gadolinium in the fluid sample. At 214, based on the concentration of gadolinium in the fluid sample, the healthcare professional determines whether the concentration of gadolinium in the fluid sample is below a concentration threshold. If so, the healthcare professional may choose not to perform resection; otherwise, the resection procedure continues back to 208.

Clause 1—A neurosurgical method for analyzing tissue at a surgical site, the method comprising: administering a contrast agent to a patient, the contrast agent including a rare earth metal for imaging a target area including tumor tissue; after administering the contrast agent, manipulating the tumor tissue with an electrosurgical instrument which generates a fluid sample from the tissue during ablation thereof; aspirating the fluid sample with an aspiration channel arranged to obtain the fluid sample from the surgical site; receiving, with a collector coupled to the aspiration channel, at least a portion of the fluid sample; measuring an absorption of a wavelength corresponding to the rare earth metal in the fluid sample with a detector; determining a concentration of the rare earth metal in the portion of the fluid sample based on the absorption; and indicating, with an indicator, presence of the rare earth metal based on the concentration of the rare earth metal.

Clause 2—A neurosurgical method for analyzing tissue at a surgical site, the method comprising: receiving at least a portion of the fluid sample with a collector coupled to an aspiration channel, the at least a portion of the fluid sample being received from the aspiration element including the aspiration channel configured to obtain the fluid sample, the fluid sample being generated by an electrosurgical instrument; heating the portion of the fluid sample in the collector with a heater to atomize the portion of the fluid sample; measuring an absorption of a wavelength corresponding to a rare earth metal with a detector; and activating, with a controller, an indicator based on the measured absorption to indicate the presence of the rare earth metal.

It will be further appreciated that the terms "include," "includes," and "including" have the same meaning as the terms "comprise," "comprises," and "comprising." Several configurations have been discussed in the foregoing description. However, the configurations discussed herein are not intended to be exhaustive or limit the invention to any particular form. The terminology which has been used is intended to be in the nature of words of description rather than of limitation.

Although several forms of the invention have been disclosed for illustrative purposes, it will be recognized that variations or modifications of the disclosed apparatus, including the rearrangement of parts, lie within the scope of the present invention.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information, but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "controller" or "module" may be replaced with the term "circuit." The term "controller" may refer to, be part of, or include: an Application Specific Integrated Circuit (ASIC); a programmable system on a chip (PSoC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits with one or more transceivers. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system may include physical and/or virtual networking equipment such as hubs, switches, routers, gateways and transceivers. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above may serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A neurosurgery system for resecting tissue at a surgical site after administration of a contrast agent to a patient, the neurosurgery system comprising:

an electrosurgical instrument configured to manipulate tissue which generates a fluid sample from the tissue during ablation thereof;

an aspiration channel arranged to obtain the fluid sample from the surgical site;

an analyzer for analyzing the fluid sample, the analyzer comprising:

a collector coupled to the aspiration channel and configured to receive at least a portion of the fluid sample from the aspiration channel;

a heater configured to atomize the portion of the fluid sample for atomic absorption spectroscopy;

a light source arranged along the collector and configured to emit light towards the atomized portion of the fluid sample such that the light passes through the collector and is absorbed by the atomized portion of the fluid sample; and a detector configured to measure an absorption of a wavelength of the light corresponding to a rare earth metal by the portion of the fluid sample;

an indicator configured to provide an indication of a presence of the rare earth metal; and a controller disposed in communication with the analyzer and the indicator and configured to instruct the indicator to provide the indication of the presence of the rare earth metal based on the measured absorption of the wavelength of the light.

2. The neurosurgery system of claim 1, wherein the rare earth metal is gadolinium.

3. The neurosurgery system of claim 1, wherein the controller is configured to determine a concentration of the rare earth metal in the portion of the fluid sample based on the measured absorption from the analyzer.

4. The neurosurgery system of claim 3, wherein the controller is configured to determine the presence or absence of tumor tissue based on the concentration of the rare earth metal in the portion of the fluid sample.

5. The neurosurgery system of claim 3, wherein the controller is configured to instruct the indicator to provide the indication based on a comparison of the concentration of the rare earth metal to a threshold.

6. The neurosurgery system of claim 1, wherein the light from the light source traverses the heater as the light passes through the collector and is absorbed.

7. The neurosurgery system of claim 6, wherein the heater is a flame and the light source is aimed at the flame.

8. The neurosurgery system of claim 1, wherein the analyzer further comprises a wavelength selector configured to receive the light passed through the collector and the heater and isolate the wavelength corresponding to the rare earth metal.

9. The neurosurgery system of claim 8, wherein the detector is coupled to the wavelength selector and is configured to detect the wavelength corresponding to the rare earth metal, measure the absorption of the wavelength to determine a concentration of the rare earth metal, and transmit a signal representative of the measured absorption.

10. The neurosurgery system of claim 1, wherein the indicator is a light source coupled to the electrosurgical instrument.

11. The neurosurgery system of claim 1, wherein the aspiration channel includes a distal end, the indicator being coupled to the aspiration channel proximally to the distal end of the aspiration channel.

12. The neurosurgery system of claim 1, wherein the electrosurgical instrument is a bipolar forceps comprising a pair of pincers, each pincer configured to function as an electrode, and wherein the bipolar forceps is adapted to generate the fluid sample from the surgical site by contacting the tissue with the pair of pincers.

13. The neurosurgery system of claim 12, wherein the aspiration channel extends along an inner portion of one of the pair of pincers.

14. The neurosurgery system of claim 12, wherein the aspiration channel extends along an outer portion of one of the pair of pincers.

15. The neurosurgery system of claim 1, wherein the electrosurgical instrument includes a distal end, and the aspiration channel includes a distal end, the distal end of the aspiration channel being positioned proximally to the distal end of the electrosurgical instrument.

16. The neurosurgery system of claim 1, wherein the electrosurgical instrument is adapted for laser ablation.

17. A neurosurgical method for analyzing tissue at a surgical site, the method comprising:

manipulating the tissue at the surgical site with an electrosurgical instrument which generates a fluid sample from the tissue;

aspirating the fluid sample with an aspiration element including an aspiration channel arranged to obtain the fluid sample;

collecting at least a portion of the fluid sample with a collector coupled to the aspiration channel;

heating the portion of the fluid sample in the collector with a heater to atomize the portion of the fluid sample;

emitting light towards the atomized portion of the fluid sample such that the light passes through the collector and is absorbed by the fluid sample;

measuring an absorption of a wavelength of the light corresponding to a rare earth metal with a detector; and activating, with a controller, an indicator based on the measured absorption of the wavelength of the light to indicate a presence of the rare earth metal.

18. The neurosurgical method of claim 17, further comprising performing a pre-operative routine to prepare for tissue analysis, wherein performing the pre-operative routine includes administering a contrast agent to a patient, the contrast agent including the rare earth metal.

19. The neurosurgical method of claim 17, wherein the rare earth metal is gadolinium and the method further comprises determining a concentration of gadolinium in the portion of the fluid sample and determining the presence or absence of tumor tissue based on the concentration of gadolinium in the portion of the fluid sample.

20. The neurosurgical method of claim 17, wherein the heater is a flame and the method comprises emitting the light towards the atomized portion of the fluid sample such that the light traverses the flame as the light passes through the collector and is absorbed.

* * * * *